(12) United States Patent
Lahti et al.

(10) Patent No.: US 7,526,339 B2
(45) Date of Patent: Apr. 28, 2009

(54) IPG CONNECTOR HEADERS FOR IMPLANTABLE MEDICAL DEVICES

(75) Inventors: Jay K. Lahti, Shoreview, MN (US); Andrew J. Ries, Lino Lakes, MN (US); Hui J. Jin, Shoreview, MN (US); David G Schaenzer, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 371 days.

(21) Appl. No.: 11/277,570

(22) Filed: Mar. 27, 2006

(65) Prior Publication Data
US 2007/0225772 A1 Sep. 27, 2007

(51) Int. Cl.
*A61N 1/00* (2006.01)

(52) U.S. Cl. ......................................................... 607/37

(58) Field of Classification Search ................... 607/36, 607/37, 38
See application file for complete search history.

(56) References Cited

U.S. PATENT DOCUMENTS

| | | | |
|---|---|---|---|
| 5,252,090 A | 10/1993 | Giurtino et al. | |
| 5,374,279 A * | 12/1994 | Duffin et al. | 607/5 |
| 5,413,595 A | 5/1995 | Stutz, Jr. | |
| 5,766,042 A | 6/1998 | Ries et al. | |
| 5,921,933 A | 7/1999 | Sarkis et al. | |
| 6,895,276 B2 | 5/2005 | Kast | |
| 2004/0116878 A1* | 6/2004 | Byrd et al. | 604/263 |
| 2004/0122481 A1 | 6/2004 | Tidemand et al. | |
| 2005/0131481 A1 | 6/2005 | Ries et al. | |
| 2005/0171509 A1 | 8/2005 | Hector | |
| 2007/0213781 A1* | 9/2007 | Fruland et al. | 607/37 |

* cited by examiner

Primary Examiner—Scott M Getzow
(74) Attorney, Agent, or Firm—Stephen W. Bauer; Scott A. Bardell

(57) ABSTRACT

IPG connector headers for implantable medical devices are provided. In one embodiment of the invention, an IPG connector header having a header bore for receiving and making electrical connection to a lead connector assembly of an implantable medical device comprises a non-conductive header base and a plurality of electrically conductive header connector elements disposed within the header base. A plurality of electrically insulative fluid seals are interposed between the header connector elements. Each fluid seal has a fluid seal bore and is formed from an elastomeric material and an additive. The additive is formulated to reduce the frictional forces required to insert the lead connector assembly through the fluid seal bores of the fluid seals.

12 Claims, 4 Drawing Sheets

IPG CONNECTOR HEADERS FOR IMPLANTABLE MEDICAL DEVICES

FIELD OF THE INVENTION

The present invention generally relates to an implantable medical device assembly, and in particular, the present invention relates to a connector assembly for making a temporary connection between a medical lead and an implantable medical device.

BACKGROUND OF THE INVENTION

Various types of devices have been developed for implantation into the human body to provide various types of health-related therapies and/or monitoring. Examples of such devices, generally known as implantable medical devices (IMDs), include cardiac pacemakers, cardioverter/defibrillators, cardiomyostimulators, various physiological stimulators including nerve, muscle, and deep brain stimulators, various types of physiological monitors, and drug delivery systems, just to name a few. For purposes of this application, reference will be made only to implantable cardiac devices and particularly to implantable cardiac pacemakers and defibrillators, it being understood that the principles herein may have applicability to other implantable medical devices as well.

An implantable medical device (IMD) may be a device such as an implantable pulse generator (IPG), commonly referred to as a pacemaker, which is used to stimulate the heart into a contraction if the sinus node of the heart is not properly timing, or pacing, the contractions of the heart. Modern cardiac devices also perform many other functions beyond that of pacing. For example, some cardiac devices such as implantable cardioverter defibrillators (ICD) may also perform therapies such as defibrillation and cardioversion as well as provide several different pacing therapies, depending upon the needs of the user or patient and the physiologic condition of the patient's heart. For convenience, all types of implantable medical devices will be referred to herein as IMDs, it being understood that the term, unless otherwise indicated, is inclusive of an implantable device capable of administering any of a number of therapies to the heart of the patient.

In typical use, an IMD is implanted in a convenient location usually under the skin of the patient and in the vicinity of the one or more major arteries or veins. One or more electrical leads connected to the IMD are inserted into or on the heart of the user, usually through a convenient vein or artery. The ends of the leads are placed in contact with the walls or surface of one or more chambers of the heart, depending upon the particular therapies deemed appropriate for the patient.

One or more of the leads is adapted to carry a current from the IMD to the heart tissue to stimulate the heart in one of several ways, again depending upon the particular therapy being delivered. The leads are simultaneously used for sensing the physiologic signals provided by the heart to determine when to deliver a therapeutic pulse to the heart, and the nature of the pulse, e.g., a pacing pulse or a defibrillation shock. Recently, bipolar and multi-polar permanently implantable pacing leads and leads for use in pacing and cardioversion/defibrillation (collectively referred to as permanent implantable cardiac leads) have been developed using coaxially arranged, coiled wire conductors and/or parallel-wound, multi-filar coiled wire conductors and having proximal lead connector assemblies coupled thereto. The proximal lead connector assemblies are formed with a proximal lead connector pin and one or more distally located ring-shaped conductive elements or lead connector rings.

The proximal lead connector assembly is inserted into the IMD so that the lead connector pin electrically contacts a connector located on a connector section affixed to the IMD. The connector section typically includes a bore containing an electrical connector that is configured to engage with a connector pin located on the proximal lead connector assembly. In addition, the connector section may comprise conductive contacts configured to contact the lead connector rings of the proximal lead connector assembly. As IMD technology progresses, the size of IMDs and associated components become increasingly reduced in size. Consequently, more conductive contacts are placed closer together in a smaller space of the connector bore. Typically, sealing rings have been used to isolate electrical contacts from one another. In addition, the sealing rings prevent fluid from entering the connector bore. However, because of the reduced IMD size, and thus, reduced sealing ring size and increased number of sealing rings employed, it has been found that, at times, when a connector end assembly is inserted into the connector section, increased insertion force is needed to press the lead connector assembly into the IMD. Similarly, increased withdrawal force is needed to remove the lead connector assembly from the connector bore.

Accordingly, it is desirable to provide an IMD with a fluid seal that permits a proximal lead connector assembly to be inserted into the connector section of the IMD with reduced insertion force. In addition, it is desirable to provide an IMD with a fluid seal that permits the proximal lead connector assembly to be withdrawn from the connector section of the IMD with reduced withdrawal force. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

In an exemplary embodiment of the present invention, an IPG connector header having a header bore for receiving and making electrical connection to a lead connector assembly of an implantable medical device is provided. The IPG connector header comprises a non-conductive header base and a plurality of electrically conductive header connector elements disposed within the header base. A plurality of electrically insulative fluid seals are interposed between the header connector elements. Each fluid seal has a fluid seal bore and is formed from an elastomeric material and an additive. The additive is formulated to reduce the frictional forces required to insert the lead connector assembly through the fluid seal bores of the fluid seals.

In another exemplary embodiment of the present invention, an IPG connector header of an IPG having an IPG housing comprising electronic circuitry is provided. The IPG connector header has a header bore for receiving and making connection to a lead connector assembly of an implantable medical device comprising a plurality of lead connector elements arranged in-line and separated by lead insulator elements. The IPG connector header comprises a non-conductive header base and a plurality of electrically conductive header connector elements disposed on the header base. Each header connector element has a connector element bore sized to receive and make electrical contact with one of the lead connector elements. The IPG connector header also comprises a plurality of electrically insulating, flexible fluid seals. Each fluid seal has a seal bore sized to receive a lead insulator element and comprises a mixture of an elastomeric material and an additive. The mixture has a durometer in the range of about 30 to 60 Shore A.

In a further exemplary embodiment of the present invention, a fluid seal having a bore for receiving a lead connector assembly of an implantable medical device and for insulating conductive connectors that electrically communicate with the lead connector assembly is provided. The fluid seal comprises an annular portion having an inside annular wall forming the bore. At least one annular ring is disposed on the inside annular wall of the annular portion and extends into the bore from the inside annular wall. The fluid seal also comprises an interlocking means for interlocking with at least one conductive connector and comprises an elastomeric material and an additive. The additive serves to reduce the frictional forces required to insert the lead connector assembly past the elastomeric material and through the bore.

BRIEF DESCRIPTION OF THE DRAWINGS

The present invention will hereinafter be described in conjunction with the following drawing figures, wherein like numerals denote like elements, and wherein.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention can be implemented in a wide variety of IMDs currently existing or that may come into existence that require the attachment of connector elements of an elongated medical lead or other elongated medical instrument with a further part of the medical device. For convenience and not by way of limitation, the present invention is described in the context of IMD comprising an IPG, which comprises a housing and a header, and electrical medical leads. Electrical feedthroughs (not shown) extending through the housing couple the electronic circuitry within the housing with one or more header connector elements that electrically and mechanically engage the lead connector elements. The electronic circuitry provides stimulation therapies through the electrodes (not shown) and/or processes signals picked up through the lead-borne electrodes and/or sensors (not shown). Thus, the term "IPG" in the specification and claims embraces pulse generators, sensors, and monitors.

Figure 1:
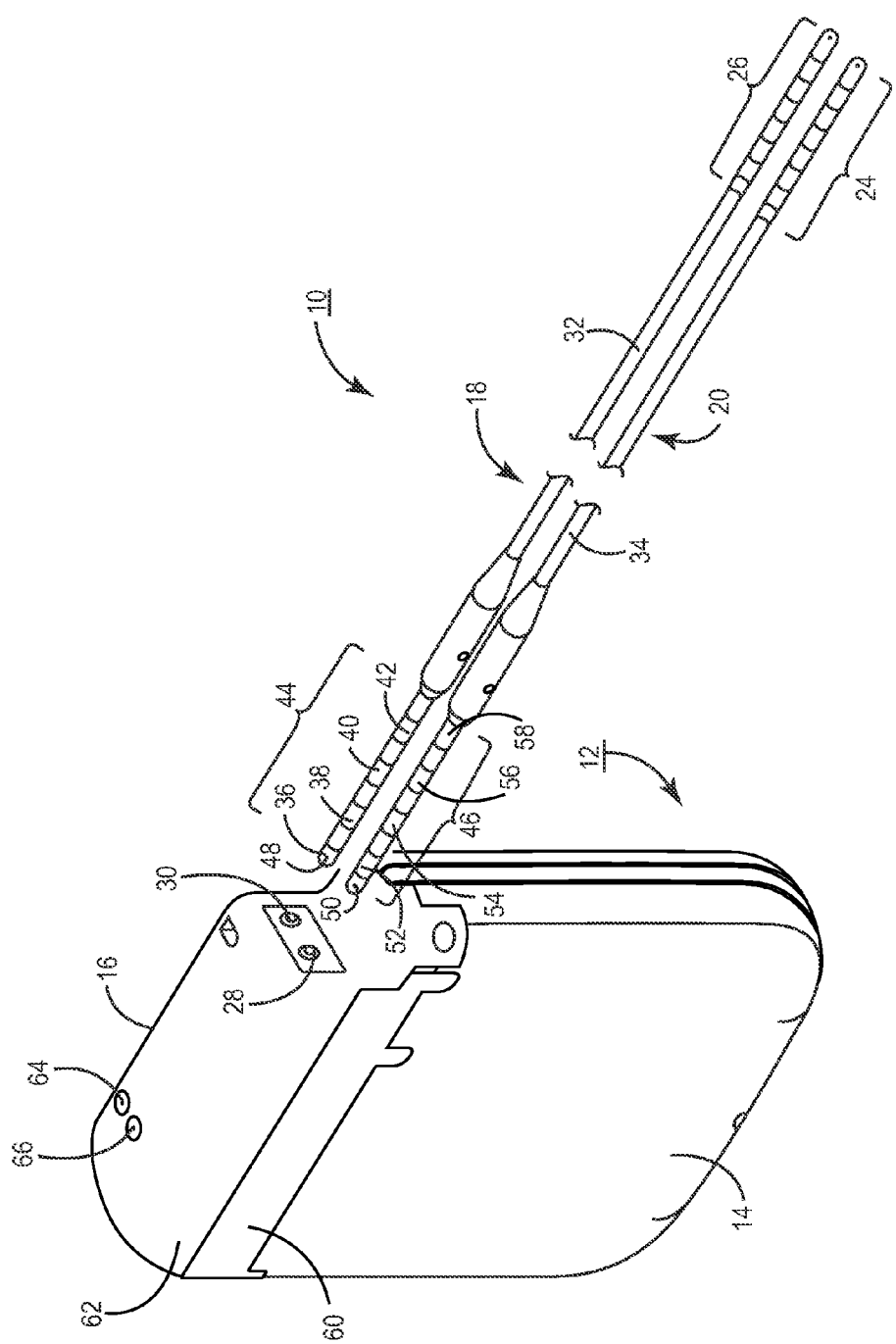
FIG. 1 schematically illustrates an IMD comprising a pair of implantable medical leads and an IPG formed of an IPG housing and an IPG header in accordance with an exemplary embodiment of the present invention.

Referring to FIG. 1, an IMD 10 in accordance with an exemplary embodiment of the present invention enables the attachment of two multi-polar electrical medical leads 18 and 20 to an IPG header 16 of IPG 12. The IMD 10 may be a neurostimulator for generating and delivering neurostimulation pulse trains to a plurality of electrodes in linear electrode arrays 24, 26 arrayed in therapeutic relation to body organs, muscles or nerves or a multi-chamber cardiac pacing system or the like.

The leads 18, 20 are depicted as to be inserted into header bores 28, 30 of the IPG header 16. The leads 18, 20 comprise elongated lead bodies 32, 34 that enclose a plurality of conductors (not shown). Four electrical conductors are electrically connected to four respective lead connector elements 36, 38, 40, 42 that are each arranged in lead connector element arrays or lead connector assemblies 44, 46 along a proximal segment of the lead bodies 32, 34 and to four electrodes in the distal electrode arrays 24, 26. While four lead connector elements and four electrodes are illustrated in FIG. 1, it will be appreciated that lead bodies 32, 34 may enclose any suitable number of conductors and may utilize any corresponding number of lead connector elements and electrodes. The lead connector elements 36, 38, 40, 42 are separated from one another and from the proximal lead tips 48, 50 by a plurality of lead insulator elements or insulation sleeves 52, 54, 56, 58. The leads 18, 20 can take the form of any electrical medical lead using conventional materials for the lead connector elements 36, 38, 40, 42 and any form of lead conductors, electrodes and/or sensors supported by the lead body 32, 34, and such particulars of the lead construction and function are not limiting of the present invention.

The IPG header 16 is formed from a preformed header base 60, a preformed header cover 62, and a pair of penetrable setscrew seals 64, 66. The head cover 62 and header base 60 enclose a pair of elongated stacks 68, 70, shown in FIG. 2, having stack bores that are axially aligned with and constitute the IPG header bores 28, 30 into which the lead connector assemblies 44, 46 are inserted.

Figure 2:
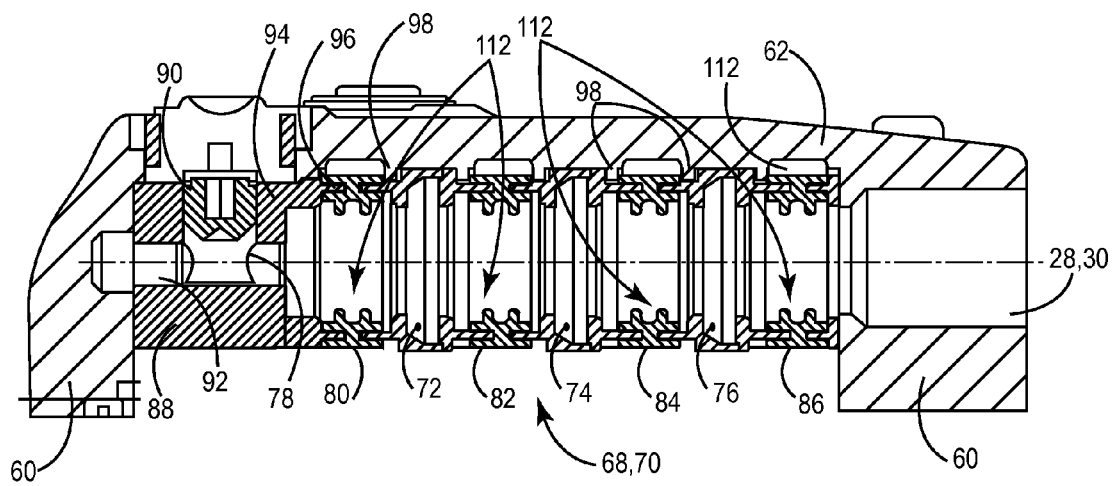
FIG. 2 is a cross-sectional view of a IPG connector stack in accordance with an exemplary embodiment of the invention.

Referring to FIG. 2, the stacks 68, 70 each comprise three header connector elements 72, 74, 76 and a setscrew connector element 78 that are each separated by tubular, elastomeric, electrically insulating, fluid seals 80, 82, 84,86. The three header connector elements 72, 74, 76, the setscrew connector element 78, and the four fluid seals 80, 82, 84, 86 are assembled in axial alignment so that the stacks 68, 70 extend through a stack length between stack proximal and distal ends. The connector elements 72, 74, 76 and setscrew connector element 78 are separated from one another by fluid seals 80, 82, 84, 86, and the stacks 68,70 provide common, elongated axial stack bores 28, 30 sized in diameter and length to receive the lead connector assemblies 44, 46.

In an exemplary embodiment of the present invention, each fluid seal 80, 82, 84, 86 is interlocked with an adjacent electrical connector element 72, 74, 76 or the setscrew connector element 78 during assembly of the stacks 68, 70 to electrically isolate the electrical connector elements 72, 74, 76 and the setscrew connector element 78 and to maintain the axial alignment and the length and diameter dimensions. In another exemplary embodiment of the present invention, the fluid seals are interposed with the electrical connector elements without interlocking. Each electrical connector element 72, 74, 76 and fluid seal 80, 82, 84, 86 has a predetermined axial length between annular ends thereof, and the combined axial length of the total number of electrical connector elements and fluid seals defines the stack length. Fluid seals 80 and 86 are located at each end of the stacks 68, 70.

Figure 3:
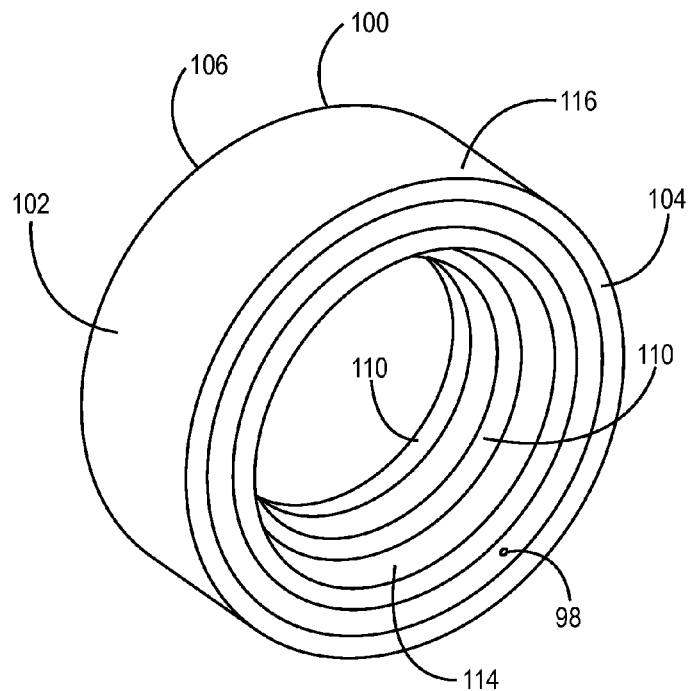
FIG. 3 schematically illustrates a fluid seal of the IPG connector stack of FIG. 2, in accordance with an exemplary embodiment of the present invention.
Figure 4:
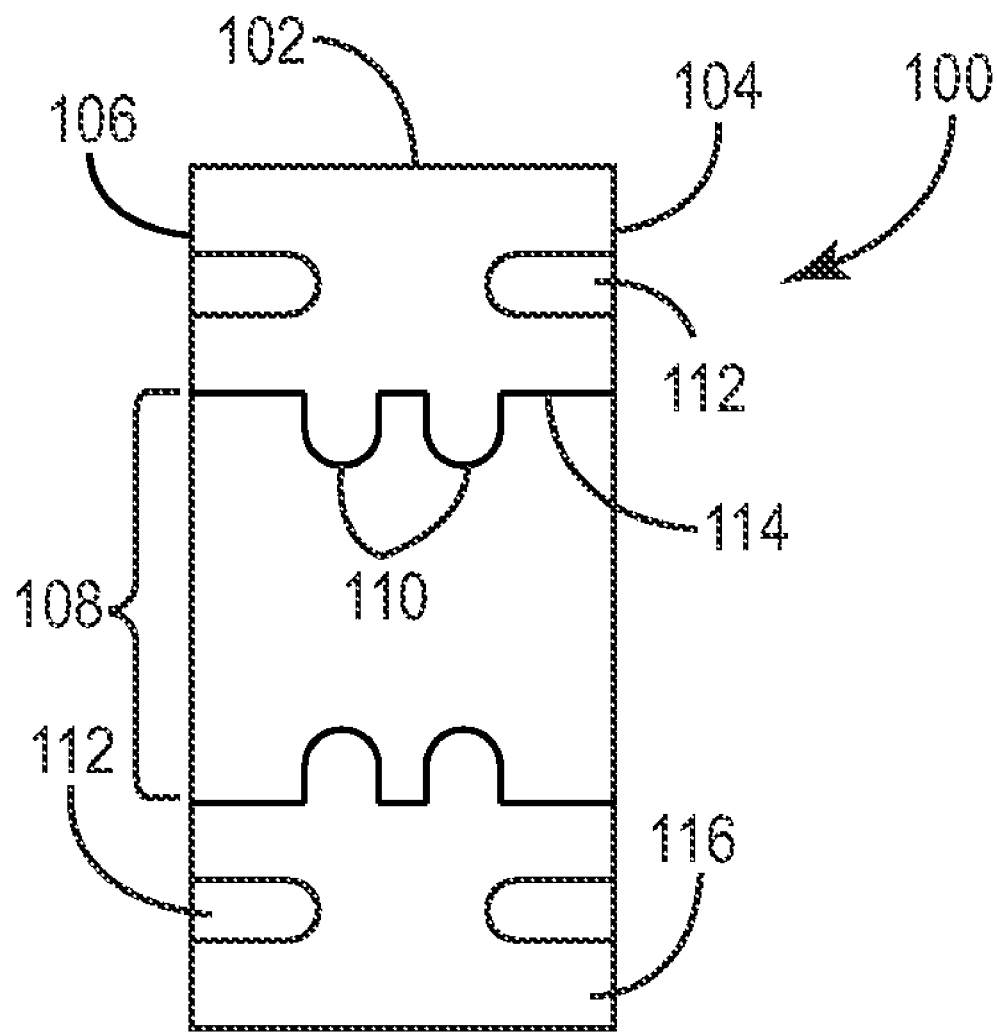
FIG. 4 is a cross-sectional view of the fluid seal of FIG. 3.

An individual fluid seal 100 among the fluid seals 80, 82, 84, 86 of FIG. 2 is shown in greater detail FIGS. 3 and 4. The fluid seal 100 has an annular portion 116 having an outside wall 102 and inside wall 114 extending between annular end walls 104 and 106 defining a fluid seal lumen or bore 108. One or more annular sealing rings 110 is formed extending from inside wall 114 inward into the seal bore 108 so that the sealing ring intrudes slightly into the stack bore 28, 30, whereby the sealing ring 110 is compressed by a lead insulator element inserted into the connector bore defined by the stack bore 28 or 30. In this manner, the sealing ring 110 of the fluid seals 80, 82, 84, 86 seals against the insulator elements 52, 54, 56, 58 to seal the stack bores 28, 30 and the electrical connections from fluid ingress. Each fluid seal has an annular female groove 112 disposed within end walls 104, 106. Each groove is configured to interlock with a male flange 98 of header connector elements 72, 74, 76 (or setscrew male flange 96). However, it will be appreciated that any suitable means for interlocking the fluid seals and the connector elements may be used. For example, the fluid seals may comprise male flanges that interlock with female grooves of the connector elements.

The fluid seal 100 is formed of a flexible elastomeric material with which has been combined with an additive that decreases the frictional forces between the fluid seal and the lead connector assemblies 44, 46 when the lead connector assemblies are inserted into the header bores 28, 30. The flexible elastomeric material of the fluid seal 100 may comprise any known or conventional elastomeric material, such as, for example, silicone, e.g., silicone rubber, enhanced tear resistant silicone (ETR), soft polyurethane, or the like. The additive may comprise any biocompatible, biostable material that does not degrade the elastomeric material and results in an external surface of the elastomeric material mixture that creates less friction than that which would result without the additive. In an exemplary embodiment of the invention, the additive is one that results in the elastomeric material mixture having a durometer in the range of about 30 to 60 Shore A. In a preferred embodiment of the invention, the additive is one that results in the elastomeric material mixture having a durometer in the range of about 35 to 50 Shore A. Examples of such additives that may be used in the present invention include, but are not limited to, titanium dioxide and barium sulfate.

Referring again to FIG. 2, as noted above, the stacks 68, 70 comprise a setscrew connector element 78 preferably located at one end of the stack 68, 70. The setscrew connector element 78 comprises a setscrew connector block 88 and a setscrew 90 fitted into a bore 94. The connector block 88 is formed with a connector element bore 92 that is axially aligned with and part of the stack bore 28, 30. The setscrew 90 and bore 94 are transverse to the connector element bore 92, and the setscrew 90 is adapted to be tightened against a segment of the lead connector assembly 44, 46 within the connector element bore 92. The setscrew connector block 88 can be used as an IPG connector element by electrical connection with the proximal lead tip 48, 50 so that the segment of the lead connector assembly 44, 46 within the connector element bore 92 comprises a lead connector element 36, 38, 40, 42. In an exemplary embodiment of the present invention, the setscrew connector block 88 is formed with an annular male flange 96 extending in parallel alignment with the stack bores 28, 30 that is fitted into an annular female groove of the tubular fluid seal 80 adjacent the setscrew connector block 88. In another exemplary embodiment, setscrew connector block 88 may be configured with a female groove and fluid seal 80 may be configured with a male flange that is interlocked into the female groove. In a further exemplary embodiment, setscrew connector block 88 may be disposed adjacent fluid seal 80 without interlocking with fluid seal 80.

Figure 5:
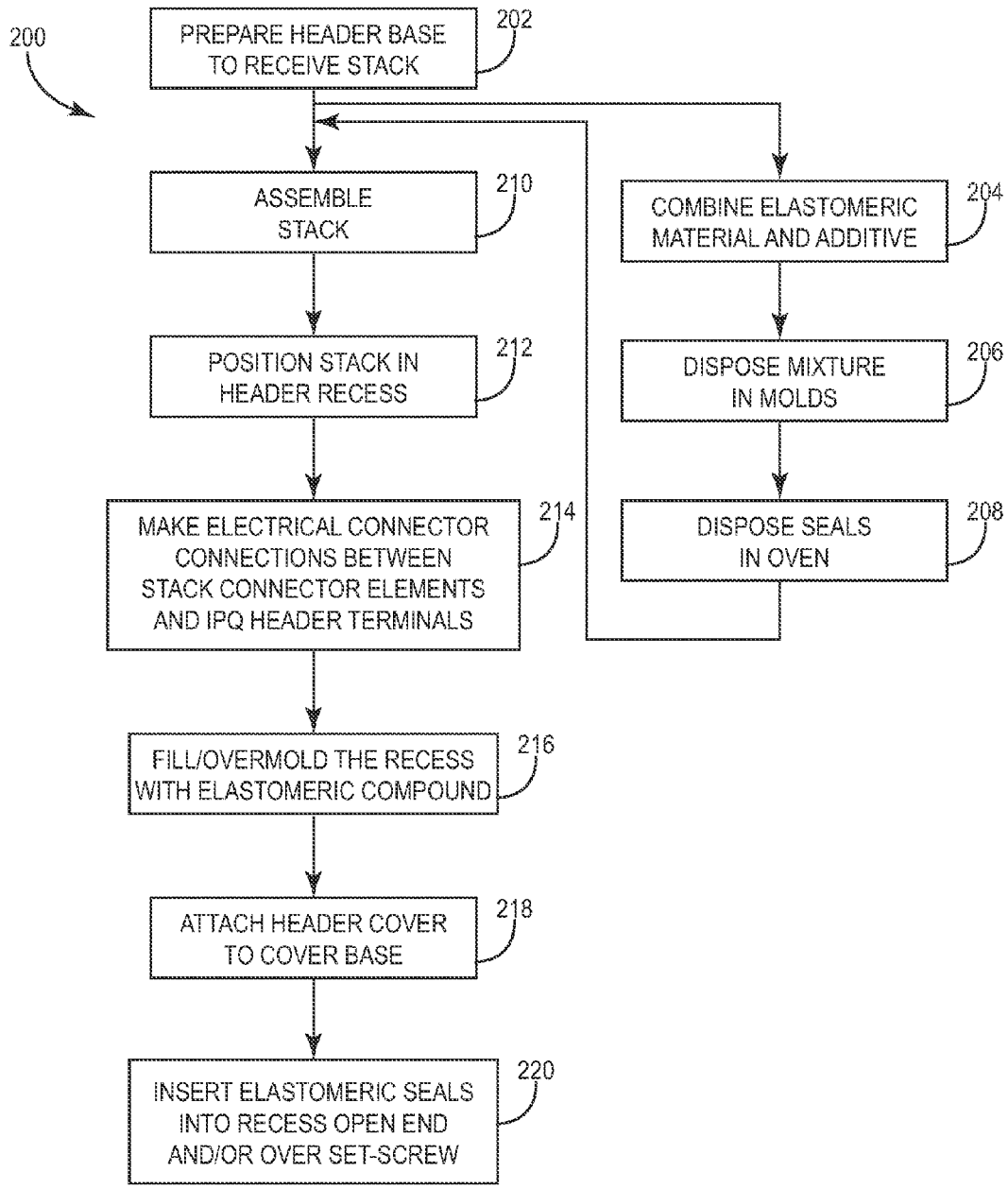
FIG. 5 is a flowchart illustrating a method for assembling an IPG header in accordance with an exemplary embodiment of the present invention.

A method 200 for assembling an IPG header incorporating stacks 68, 70 is illustrated in FIG. 5. The method includes preparing a pre-molded header base 60 (step 202). The fluid seals 80, 82, 84, 86 are fabricated by combining the additive uniformly with the elastomeric material (step 204). The step of combining may be performed using any conventional method of mixing, such as, for example, by stirring with a mechanical stirrer or by agitating with a mechanical additive. In an exemplary embodiment of the present invention, if the additive is titanium dioxide, the additive is combined with the elastomeric material in an amount of about no greater than 2.5% by weight in relation to the elastomeric material. In a preferred embodiment of the present invention, the titanium dioxide is combined with the elastomeric material in an amount of about less than 2.0%±0.2% by weight in relation to the elastomeric material. In another exemplary embodiment of the present invention, if the additive is barium sulfate, the additive is combined with the elastomeric material in an amount of about no greater than 15% by weight in relation to the elastomeric material. In a preferred embodiment of the present invention, the barium sulfate is combined with the elastomeric material in an amount of about 12.5%±2.5% by weight in relation to the elastomeric material.

After combining the elastomeric material and the additive, the mixture is disposed into molds, such as injection molds, which have been manufactured in accordance with the predetermined dimensions of the fluid seal and have been heated (step 206). The mixture is allowed to at least partially cure in the molds. After partial or substantial curing, the molded seals are disposed in a heated oven until substantially or fully cured (step 208). In an exemplary embodiment of the invention, the oven may be heated to a temperature in the range of about 300 to about 400° F. After curing, the fluid seals may be used to manufacture the elongated stacks of the IMD header.

The stacks 68, 70 then are assembled, as described above (step 210). The stacks 68, 70 are fitted into respective side-by-side cavities or recesses or a single enlarged cavity or recess of header base 60 (step 212). In IPG headers designed to have a single IPG header bore, only one such stack is inserted into the header base 60. Electrical conductors, e.g. an array of preformed Niobium ribbons, are inserted into slots of the header base 60 and their free ends are welded to the connector elements 36, 38, 40, 42 of the stacks (step 214). The exposed stacks 68, 70 are over-molded or back-filled with an elastomeric compound, e.g., silicone rubber, to fill the remaining space of the recess or recesses and present a finished outer surface (step 216).

In an exemplary embodiment, a header cover 62 formed of the same material as the header base 60 is then fitted over and adhered to the over-molded assembly, e.g., by ultrasonic welding of the edges of the cover 62 to the base 60 (step 218). The cover 62 can be first fitted over the openings of the recesses and stacks 68, 70 and liquid polymer injected into the remaining space of the recess or recesses. Penetrable seals 64, 66 are fitted into an opening of the header cover 62 and adhered thereto over the setscrews 90 that are penetrated by a hex wrench or other shaped tool to engage and rotate the setscrews 90 (step 220).

Accordingly, an IMD with a fluid seal that permits a connector end assembly to be inserted into the connector section of the IMD with reduced insertion force has been described. In addition, an IMD with a fluid seal that permits the connector end assembly to be withdrawn from the connector section of the IMD with reduced withdrawal force also has been described. While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

The invention claimed is:

1. An IPG connector header having a header bore for receiving and making electrical connection to a lead connector assembly of an implantable medical device, the IPG connector header comprising:
   a non-conductive header base;
   a plurality of electrically conductive header connector elements disposed within the header base;
   a plurality of electrically insulative fluid seals interposed between the header connector elements, wherein each fluid seal has a fluid seal bore and comprises a mixture of an elastomeric material and barium sulfate, the barium sulfate present in an amount of from about 10 to about 15 weight percent based on the weight of the elastomeric material.

2. The IPG connector header of claim 1, wherein the elastomeric material comprises one selected from the group consisting of silicone, enhanced tear resistant silicone, and polyurethane.

3. The IPG connector header of claim 1, wherein the additive and the elastomeric material comprise a mixture having a durometer in the range of about 30 to about 60 Shore A.

4. The IPG connector header of claim 3, wherein the mixture has a durometer in the range of about 35 to 50 Shore A.

5. An IPG connector header of an IPG having an IPG housing comprising electronic circuitry, wherein the IPG connector header has a header bore for receiving and making connection to a lead connector assembly of an implantable medical device comprising a plurality of lead connector elements arranged in-line and separated by lead insulator elements, wherein the IPG connector header comprises:
   a non-conductive header base;
   a plurality of electrically conductive header connector elements disposed on the header base, each having a connector element bore sized to receive and make electrical contact with one of the plurality of lead connector elements; and
   a plurality of electrically insulating, flexible fluid seals, each having a seal bore sized to receive a lead insulator element, wherein each of the plurality of fluid seals comprises a mixture of an elastomeric material and barium sulfate, the barium sulfate present in an amount of from about 10 to about 15 weight percent based on the weight of the elastomeric material, and wherein the mixture has a durometer in the range of about 30 to 60 Shore A.

6. The IPG connector header of claim 5 wherein the mixture has a durometer in the range of about 35 to 50 Shore A.

7. The IPG connector header of claim 5, wherein the barium sulfate being present in an amount no greater than about 2.5% by weight in relation to the elastomeric material.

8. The IPG connector header of claim 5, wherein the elastomeric material comprises silicone, enhanced tear resistant silicone, or polyurethane.

9. A fluid seal having a bore for receiving a lead connector assembly of an implantable medical device and for insulating conductive connectors that electrically communicate with the lead connector assembly, wherein the fluid seal comprises:
   an annular portion having an inside annular wall forming the bore;
   at least one annular ring disposed on the inside annular wall of the annular portion and extending into the bore from the inside annular wall; and
   interlocking means for interlocking with at least one conductive connector, wherein the fluid seal comprises a mixture of an elastomeric material and barium sulfate, the barium sulfate present in an amount of from about 10 to about 15 weight percent based on the weight of the elastomeric material, and wherein the additive serves to reduce the frictional forces required to insert the lead connector assembly past the elastomeric material and through the bore.

10. The fluid seal of claim 9, wherein the elastomeric material comprises one selected from the group consisting of silicone, enhanced tear resistant silicone, and polyurethane.

11. The fluid seal of claim 9, wherein the additive and the elastomeric material comprise a mixture having a durometer in the range of about 30 to about 60 Shore A.

12. The fluid seal of claim 11, wherein the mixture has a durometer in the range of about 35 to 50 Shore A.

* * * * *